| United States Patent [19] | [11] | Patent Number: | 4,762,854 |
|---|---|---|---|
| Lloyd et al. | [45] | Date of Patent: | Aug. 9, 1988 |

[54] METHOD OF REDUCING URINE PH

[75] Inventors: William E. Lloyd; Daniel J. Sullivan, both of Shenandoah, Iowa

[73] Assignee: Vet-A-Mix, Shenandoah, Iowa

[21] Appl. No.: 937,475

[22] Filed: Dec. 2, 1986

Related U.S. Application Data

[63] Continuation of Ser. No. 821,524, Jan. 24, 1986, abandoned, which is a continuation of Ser. No. 666,751, Oct. 31, 1984, abandoned.

[51] Int. Cl.$^4$ .............................................. A61K 31/19
[52] U.S. Cl. .................................................... 514/557
[58] Field of Search ......................................... 514/557

[56] References Cited

U.S. PATENT DOCUMENTS 4,100,160  7/1979  Walser .................................. 424/317

OTHER PUBLICATIONS

Chemical Abstracts 100:33628x (1983).

*Primary Examiner*—Leonard Schenkman
*Attorney, Agent, or Firm*—Larson and Taylor

[57] ABSTRACT

(2-hydroxy-4-methylthio) butyric acid and pharmaceutically acceptable salts thereof are found to effectively reduce urine pH in mammals without toxic effects.

4 Claims, 2 Drawing Sheets

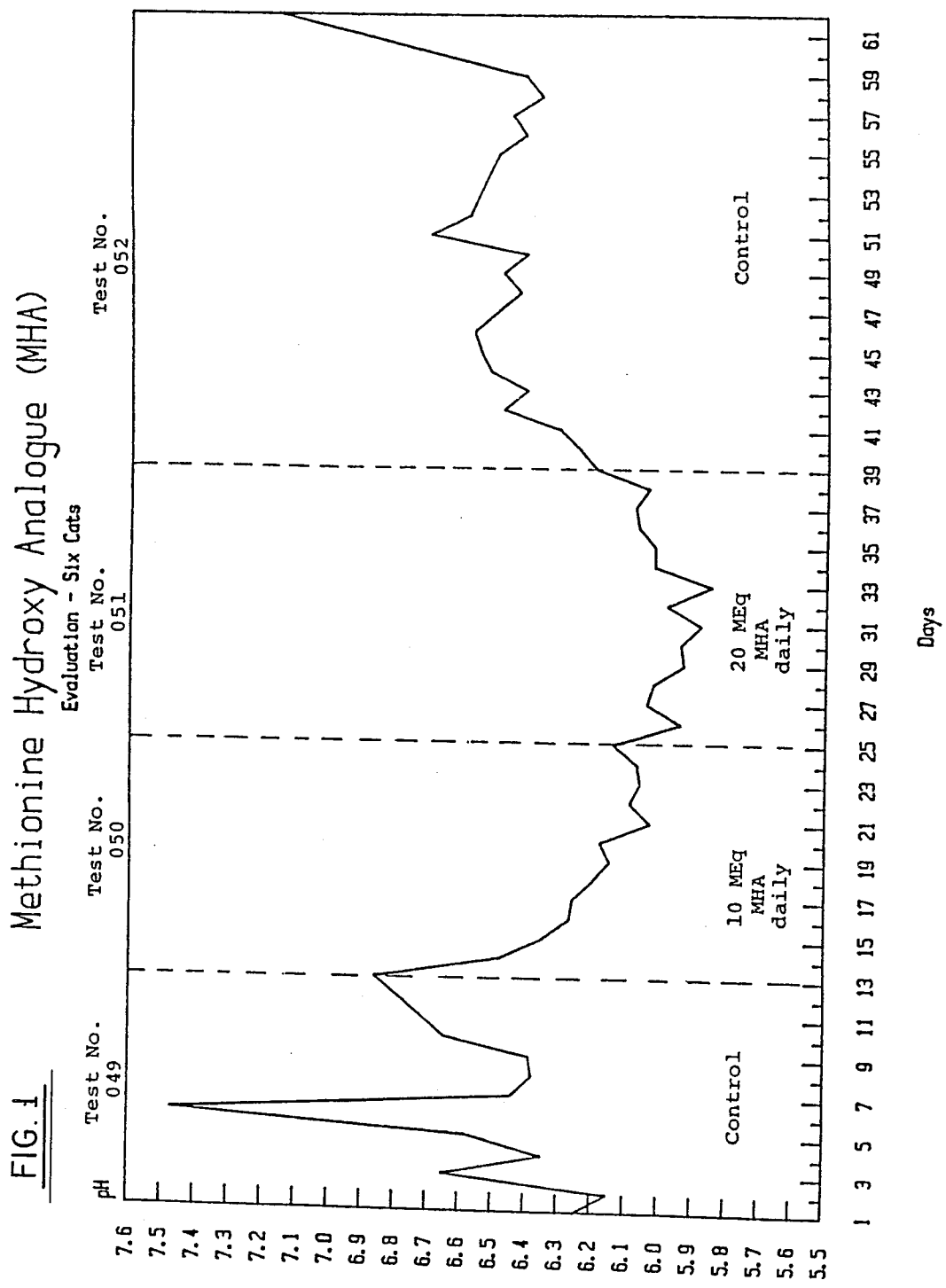

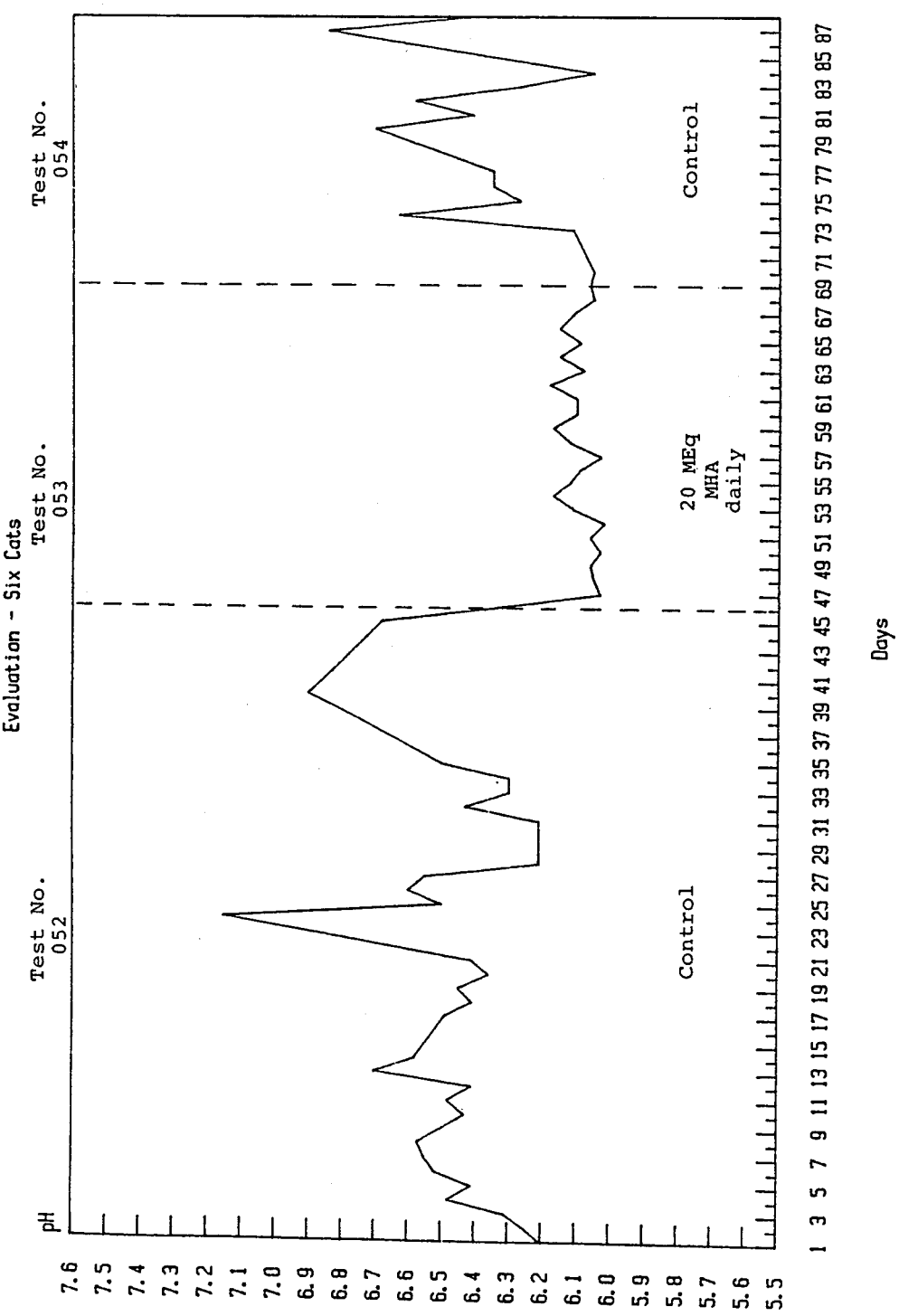

METHOD OF REDUCING URINE PH

This application is a continuation of application Ser. No. 821,524, filed Jan. 24, 1986, which is a continuation of Ser. No. 666,751, filed Oct. 31, 1984, both now abandoned.

FIELD OF THE INVENTION

This invention relates to the administration of urinary acidifiers to mammals. More particularly, this invention is directed to an improved method of reducing urine pH in mammals by administering thereto (2-hydroxy-4-methylthio) butyric acid and pharmaceutically acceptable salts thereof as the urinary acidifier.

BACKGROUND OF THE INVENTION

Urinary acidifiers have been commonly used to acidify the urine of mammals for the purpose of preventing or eliminating urinary crystalloid formation. For example, urinary acidifiers have been widely prescribed by veterinarians to aid in the treatment and prevention of feline urological syndrome (FUS). This condition, characterized by cystitis, urolithiasis, urethritis and urethral blockage, accounts for 10% of the total disease seen in adult male cats. Urethral blockage, moreover, produces extra-renal uremia with elevated blood urea nitrogen (BUN), hyperphosphatemia, hyperkalemia, metabolic acidosis, and death if not treated. Although conclusive data supporting the relationship of urine pH and FUS does not exist, urine acidifiers, nevertheless, are employed to reduce supersaturation of urinary crystalloids and the formation of uroliths. One of the principles suggested for reducing the concentrations of urinary crystalloids is to increase their solubility by reducing urinary pH.

Two of the more popular urinary acidifiers employed at the present time are methionine and ammonium chloride. These compounds have been used to acidify urine in mammals, theoretically by production of sulfuric and hydrochloric acids, respectively. However, both compounds break down and produce ammonia in the body, a compound which is toxic until it is rendered relatively non-toxic by conversion to urea, predominantly in the liver. Excess ammonia is particularly undesirable in mammals with liver and kidney disease. Poorly functioning livers may not efficiently convert ammonia to urea, allowing accumulation of ammonia in the peripheral blood stream, with a resultant hyperammonemia and hepatic encephalopathy. Poorly functioning kidneys may not be able to excrete the excess urea and ammonia caused by administering excess methionine and ammonium chloride, thus contributing to the uremia and hyperammonemia.

Another factor favoring a urinary acidifier which does not release ammonia is the fact that some kidney stones are composed of struvite, a complex compound containing magnesium, ammonium and phosphate. Most commonly used acidifiers such as dl-methionine, ammonium chloride and potassium and sodium phosphates contribute to the body burdens of ammonia and phosphates.

It is an object of the invention, therefore to effectively acidify the urine of mammals such as cats, dogs, pigs, rats, humans and other monogastric mammals, without the usual toxic and undesirable side effects that accompany other commonly employed urinary acidifiers.

Another object of the invention is to effectively prevent or reduce the concentrations of urinary crystalloids in the urine of mammals by treating the mammal with a urinary acidifier that does not yield ammonia as a metabolite.

SUMMARY OF THE INVENTION

These and other objects of the invention are obtained by reducing or preventing the concentration of urinary crystalloids in the urine of mammals by administering to the mammal, 2-hydroxy-4-(methylthio) butyric acid and pharmaceutically acceptable salts thereof in amounts effective to reduce the urine pH. The urinary acidifier of the invention is also known as methionine hydroxy analogue (MHA).

DETAILED DESCRIPTION OF THE INVENTION

The amount of the urinary acidifier of the invention (hereinafter referred to as MHA) administered in any given case will vary depending principally upon the particular mammal being treated, its metabolic body size and the increase in urine acidity desired. Any of the methods known in the prior art as, for example, methods employing trial-and-error dose/response relationship, can be used to determine the dosage. In such methods, a known dose is first given and, if the pH of the urine is lowered to desired level, the amount given is the "dose". Prior research with other widely used urinary acidifiers such as dl methionine and ammonium chloride and a combination thereof, demonstrated that dosage based on the milliequivalent weight of the urinary acidifier yielded a predictable response. For instance, 6.7 milliequivalents (500 mg) of dl methionine lowered feline pH levels to 6.37 and 20 milliequivalents (1500 mg) of dl methionine lowered the mean urine pH value to 6.01. This latter pH level is considered by experts in the field to be adequate for the prevention of urolith formation.

The urinary acidifier can be administered either in its acid form or in the form of a pharmaceutically acceptable salt such as an alkaline earth metal salt, an alkali salt and the like. The preferred alkaline earth metal salt is calcium and the preferred alkali metal salt is sodium.

Administration of the urinary acidifier to the mammals treated can be by any of the conventional methods. Preferably the urinary acidifier is administered in daily doses as chewable tablets or by mixing the drugs, in powdered form, in food. For the smaller mammals such as cats and dogs chewable tablets at daily dosages of 500, 1000 or 1,500 mg have been found most convenient. Daily administration of the urinary acidifier for several days, depending upon the particular mammal treated, is normally necessary to maintain continuous effects. In cats, for instance, approximately 2 days of dosing is usually required to obtain the maximum effects.

IN THE DRAWINGS

FIG. 1 is a plot of the urine pH data obtained in the measurements of Example I; and FIG. 2 is a plot of the urine pH data obtained in the measurements of Example II.

EXAMPLE I

Six adult male cats were administered 10 milliequivalents of MHA calcium salt daily for eleven consecutive days and the urine pH was recorded each day. After this period the daily dosage was increased by 10 milliequivalents. Daily measurements of the urine pH were similarly taken. The determination of the desired dosage was calculated as follows:

The formula weight of the ½ calcium salt of MHA is 169.22. The chemical formula is $CH_3S(CH_2)_2CHOH\text{-}COO\ Ca.\frac{1}{2}$. It was postulated that the sulfur atom will be metabolized to $H_2SO_4$ or that 1 sulfur atom will yield 2 hydrogen atoms. Therefore, 1 millimole of MHA (0.16922 g) will yield 1 millimole of $H_2SO_4$ or 2 milliequivalents. So 1 milliequivalent of MHA=0.16922/2=0.0846 g. Ten milliequivalents is therefore equal to 0.846 g and twenty milliequivalents is twice this amount or 1.692 g.

The results of the tests, designated 050 and 051, are listed in Table 1 and graphed in FIG. 1, respectively.

The control test designated 049 preceded test 050. This test was conducted for twelve consecutive days. The mean urine pH from the urine samples are listed in Table 1 below. The pH data plotted each day are displayed in FIG. 1. Also, a second control test (052) was initiated by withdrawing the dosage of MHA and continued for twenty two days. The results are also reported in Table 1 and the graph of FIG. 1.

TABLE 1

| Urinary pH in six cats dosed with Methionine Hydroxy Analogue | | | | |
|---|---|---|---|---|
| Test No. | Dose | No. of Samples | $\bar{x}$ pH* | s+ |
| 049 | Control | 44 | 6.59 | .462 |
| 050 | 10 mEq | 54 | 6.20 | .338 |
| 051 | 20 mEq | 64 | 6.00 | .139 |
| 052 | Control | 90 | 6.47 | .400 |

*Mean values
+Standard deviation

The results show that Methionine Hydroxy Analogue (MHA) is an effective urinary acidifying agent in male cats. Ten milliequivalents reduced the urinary pH from 6.59 to 6.20 in approximately (ca) 5 days and maintained the urine acidity at this level for the balance of the test duration (ca 7 days). The ΔpH or change in acidity was 0.39. The resultant lowered pH value represents a hydrogen ion concentration of 245% of the control value.

Twenty milliequivalents of MHA reduced the urinary pH further to 6.00, or a hydrogen ion concentration of $1 \times 10^{-6}$. The control pH was 6.59, or a hydrogen ion concentration of $2.57 \times 10^{-7}$. The hydrogen ion concentration in cat urine after treatment was 389% of control values.

EXAMPLE II

The same 6 adult male cats described in Example I were given 20 milliequivalents of MHA ½ calcium salt (1.69 g) daily for 22 days immediately after a 42 day "control" period. Within 48 hours, mean urine pH dropped to 6.09 and remained at this approximate value for 20 days when the dosage was discontinued. The results of these tests, designated #052 and #053 respectively, are listed in Table 2 and graphed in FIG. 2.

TABLE 2

| Urinary pH in six cats dosed with Methionine Hydroxy Analogue | | | | |
|---|---|---|---|---|
| Test No. | Dose | No. of Samples | $\bar{x}$ pH* | s+ |
| 052 | Control | 90 | 6.47 | .400 |
| 053 | 20 mEq | 100 | 6.09 | .150 |
| 054 | Control++ | 28 | 6.52 | .512 |

*Mean values
+Standard deviation
++Still ongoing

This repeat of the 20 milliequivalent portion of the MHA trials also reduced pH approximately the same value. The means pH value obtained was 6.09.

I claim:

1. In a method of reducing or preventing the concentration of urinary crystalloids in the urine of mammals in need thereof by the administration thereto of a urinary acidifier in amounts effective to reduce the urine pH to a level that reduces or prevents the concentration of urinary crystalloids, the improvement comprising selecting as the urinary acidifier 2-hydroxy-4-(methylthio) butyric acid and pharmaceutically aceptable salts thereof.

2. A method according to claim 1 wherein the mammal is a cat.

3. A method according to claim 1 wherein the mammal is a dog.

4. A method according to claim 1 wherein the mammal is a human.

* * * * *